United States Patent [19]

Kontorovich

[11] Patent Number: 5,439,826
[45] Date of Patent: Aug. 8, 1995

[54] METHOD OF DISTINGUISHING AMONG STRIPS FOR DIFFERENT ASSAYS IN AN AUTOMATED INSTRUMENT

[75] Inventor: Michael Kontorovich, Colchester, Vt.

[73] Assignees: Bio-Tek Instruments, Inc., Winooski, Vt.; Syva Company, Palo Alto, Calif.

[21] Appl. No.: 278,902

[22] Filed: Dec. 2, 1988

[51] Int. Cl.$^6$ ............................................. G01N 35/02
[52] U.S. Cl. .................................... 436/50; 422/63; 422/66; 422/67; 422/105; 436/44; 436/46; 436/49; 436/55; 436/164; 436/172
[58] Field of Search ................ 436/518, 43, 528, 430, 436/531, 805, 50; 422/63, 52, 55, 67

[56] References Cited

U.S. PATENT DOCUMENTS

| | | | |
|---|---|---|---|
| 3,907,503 | 9/1975 | Betts et al. | 422/67 |
| 4,135,883 | 1/1970 | McNeil et al. | 422/72 |
| 4,476,149 | 10/1984 | Poppe et al. | 427/2 |
| 4,592,893 | 6/1986 | Poppe et al. | 422/56 |

FOREIGN PATENT DOCUMENTS

| | | |
|---|---|---|
| 0073056 | 8/1982 | European Pat. Off. . |
| WO8300393 | 2/1983 | European Pat. Off. . |
| 0210014 | 1/1987 | European Pat. Off. . |
| 0243915 | 4/1987 | European Pat. Off. . |
| 8300393 | 2/1983 | WIPO . |

OTHER PUBLICATIONS

European Search Report (1988).

*Primary Examiner*—Glennon H. Hollrah
*Assistant Examiner*—Brian M. Burn
*Attorney, Agent, or Firm*—Sughrue, Mion, Zinn, Macpeak & Seas

[57] ABSTRACT

A method of distinguishing between strips for different assays in an automated instrument, wherein characteristics to which the instrument is sensitive are selectively introduced in microwells of individual microstrips which are pretreated with a specific antigen or antibody for a particular test. On each microstrip, the wells having the characteristic collectively define a multi-bit code which corresponds to a particular condition or disease to be tested for. The automated instrument reads the characteristic from the selected wells and thus determines what test is to be conducted. The marks may have optical, radioactive, luminescent, fluorescent, or magnetic characteristics, in accordance with the test to be conducted.

18 Claims, 3 Drawing Sheets

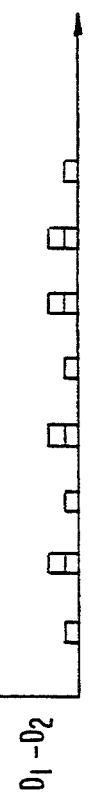
FIG.6A
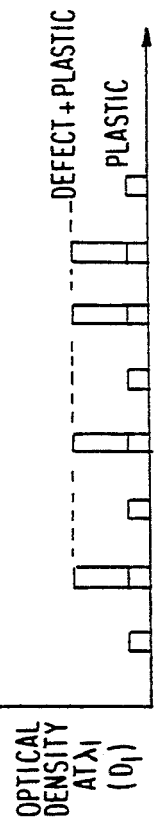
FIG.6B
FIG.6C
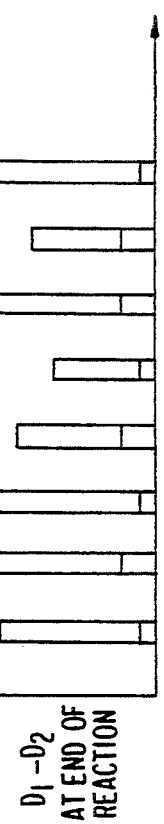
FIG.6D
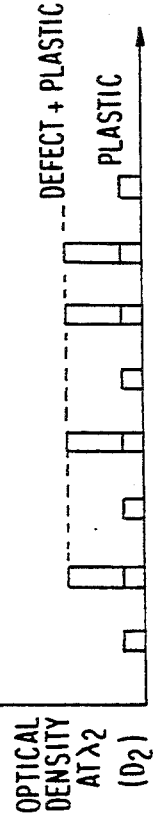
FIG.6E
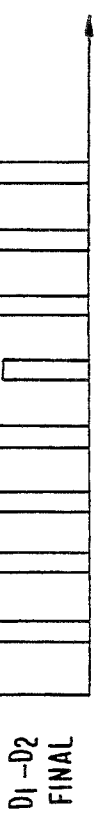
FIG.6F

METHOD OF DISTINGUISHING AMONG STRIPS FOR DIFFERENT ASSAYS IN AN AUTOMATED INSTRUMENT

BACKGROUND OF THE INVENTION

The present invention relates to an improved method for performing automated immunoassays, and in particular to performance of enzyme-linked immunosorbent assays (ELISA). Methods of automating ELISA are known, as disclosed for example in U.S. Pat. No. 4,708,929. Such automated techniques may involve detection of fluorescence, reflectance, optical density, radioactivity, and other physical characteristics.

In performing such assays, samples to be tested are introduced into individual microwells within a microstrip or microplate. One example of a microstrip is shown in FIG. 1A. Each microstrip may optionally be placed in a holder, as shown in FIG. 2A. A plurality of microstrips are placed in a carrier, the carrier then being inserted into the instrument. The instrument, which may measure one of the above-measured characteristics, is focused on the microwells in a given microstrip, and corresponding data derived from the read-out of the device (as a function of optical density, radioactivity, etc.). The data which is derived from the device read-out identifies the presence or absence of a given analyte (for example, HIV or clamydia).

Conventionally, at the beginning of the test, an operator of the device will input information (via a keyboard or other means) to tell the instrument what analyte is being tested for, so that the read-out may be correlated appropriately with a reference. For example, if the test is being conducted to determine the presence of chlamydia in the samples, the read-out should be correlated with a reference value corresponding to presence of chlamydia in the sample.

Because operator input is required, the degree of automation of the operation is less than complete. Also, since the strips are not visually or otherwise distinguishable once they are pretreated with a specific analyte, operator error is possible. It would be desirable to automate the process yet further, by providing identification of what disease is to be tested for in a particular strip, without the need for operator interaction.

SUMMARY OF THE INVENTION

In view of the foregoing, it is an object of the present invention to provide a method of automatically identifying, to an automated testing device, a analyte for which the test is to be conducted. In the method according to one embodiment of the invention, this is done conveniently by providing a coded identification on the microstrip itself. The identification is provided by introducing a defect, or other type of indication consistent with the type of test being conducted. For example, in the best mode presently known to the inventors, when optical density is being measured in the various samples of a microstrip, a series of marks (which may be generated in any number of ways) may be provided selectively on the bottom of the various microwells of the microstrip. When the testing device then reads the data on the bottom of the different microwells, there is a multi-bit indication of what analyte is being tested for, one bit for each microwell.

Another way of providing a similarly useful coded indication is to treat the contents of the wells themselves with a chemical which introduces an identifiable characteristic which the testing instrument can detect. The chemical then can be removed from the sample during one of the testing steps.

It is contemplated that the method of the invention is applicable to introduction of any type of defect (for example, radioactivity, magnetic indications or the like) into the microwells of the microstrip for detection and identification by the testing device. Implementation of this approach would be similar to that for the optical density situation.

BRIEF DESCRIPTION OF THE DRAWINGS

The foregoing and other objects of the present invention will be described with reference to the accompanying drawings, in which:

FIGS. 6A–6F show optical density characteristics for marked and unmarked wells of a microstrip, and effects of cancellation of defects in the microstrips.

DETAILED DESCRIPTION OF THE PREFERRED EMBODIMENT

Figure 3:
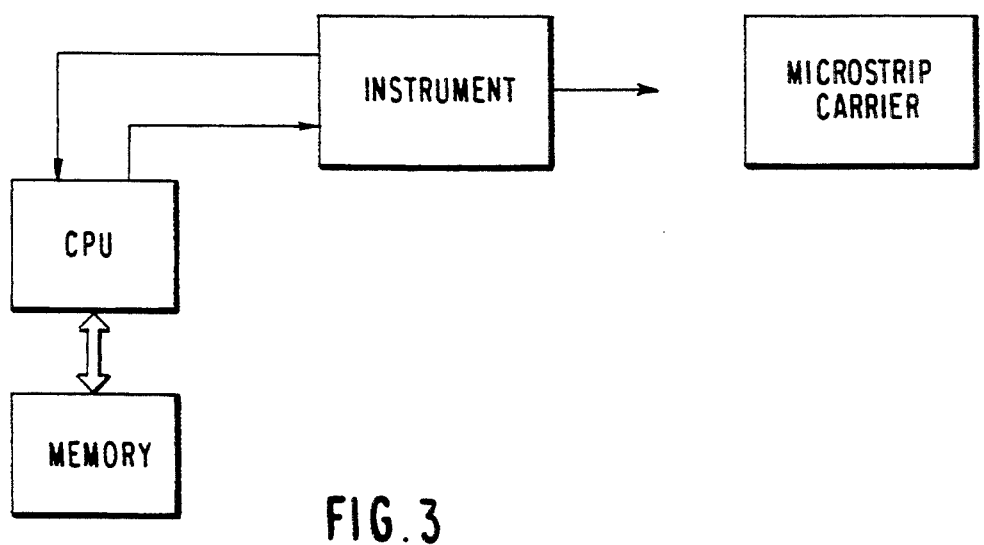
FIG. 3 shows a schematic representation of an apparatus capable of implementing the method of the present invention.

A preferred implementation of the present invention now will be described in detail, with reference to the accompanying drawings, FIG. 3 of which shows an automated measuring device which employs a spectrophotometer. One example of such an instrument is the BIO-TEK EL309 Autoreader. However, the method also may be practiced advantageously in any automated instrument. As noted above, the method of the invention is usable in other types of automated instruments for conducting other tests in which different physical characteristics, such as radioactivity, fluorescence, etc. are measured.

Figure 1A:
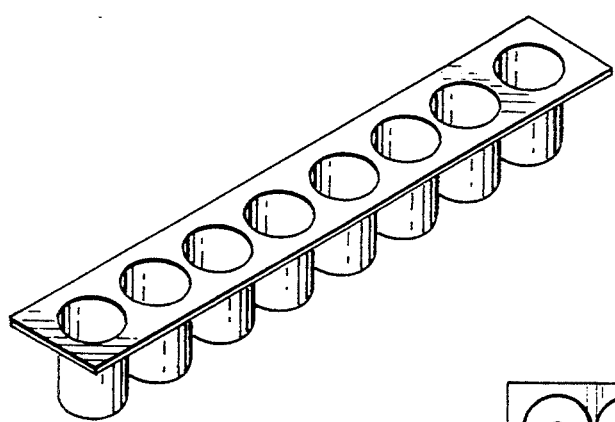
FIG. 1A shows a sample of a conventional microstrip.
Figure 1B:
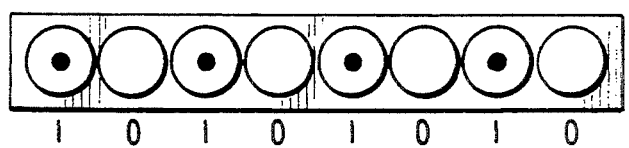
FIG. 1B shows a microstrip on which indications have been placed in accordance with the method of the present invention.

One example of a microstrip bearing suitable characteristic markings is shown in FIG. 1B. Microstrips vary among manufacturers, some microstrips having different numbers and sizes of wells, the wells being separated by different amounts, and having flat or round bottoms. There are microstrips with single and double rows of wells, and the invention is practicable as to these as well. For purposes of describing the preferred embodiment, an example of a single-row, eight-well microstrip will be used. However, it should be understood that the invention is not limited to such an example.

The strips themselves are pretreated with a specific antigen or specific antibody (when ELISA is used) to determine presence or absence of a given analyte. Referring to the above example, the strips are arranged in sets of 12 within a carrier, thus forming an 8 by 12 matrix of wells with a total of 96 wells.

At this point, it is appropriate to discuss some background behind the reading of microstrips using an optical density technique. To implement this technique, light is shined through the wells, and the amount of light passing through is measured. Different chemical solutions exhibit different optical density characteristics, and different absorbence spectra, as a function of the wavelength of light used. Artifacts on the microstrips themselves, such as fingerprints, dents, smudges, scratches, etc., can affect these spectra. From experience, it has been determined that at some wavelengths, the observed spectra are a function of both the solutions and the artifacts/imperfections, while at other wavelengths, the observed spectra are a function only of the artifacts.

In view of the foregoing, dual-wavelength techniques for measuring optical density have been implemented. For example, looking at FIGS. 5A and 5B, absorbence spectra, including optical density values at wavelengths $\lambda_1$ and $\lambda_2$, are respectively shown. The optical density value at wavelength $\lambda_1$ is affected by both the solution involved and the artifacts present in the microstrip. In the case of optical density, the presence of artifacts causes a higher optical density reading. The optical density value at wavelength $\lambda_2$ is affected only by the presence of artifacts. Ideally it is desired that $D(\lambda_1) >> D(\lambda_2)$ for the solution, and $D(\lambda_1) = D(\lambda_2)$ for the artifacts (where D connotes optical density). By subtracting the value for $\lambda_2$ from that for $\lambda_1$, a value which is a function only of the solution is derived. That derived optical density value then can be compared with reference values and presence or absence of a particular analyte can be made.

Figure 5A:
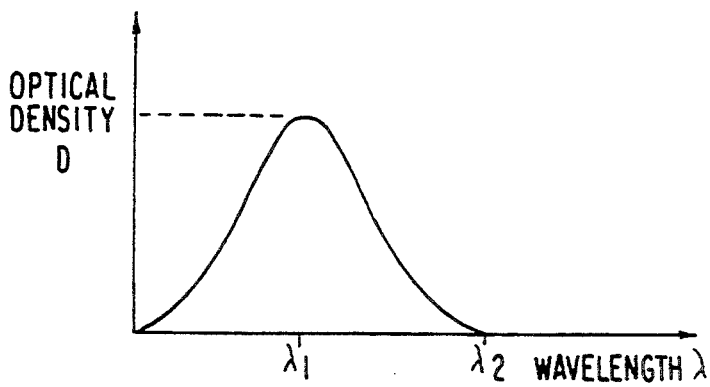
FIGS. 5A, 5B, and 5C show graphs of absorbence spectra for a given solution, for artifacts present in a microstrip, and for the sample and artifacts combined.
Figure 5B:
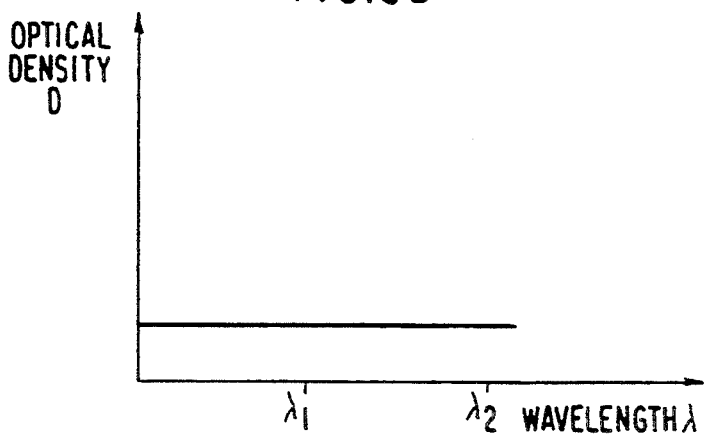
Figure 5C:
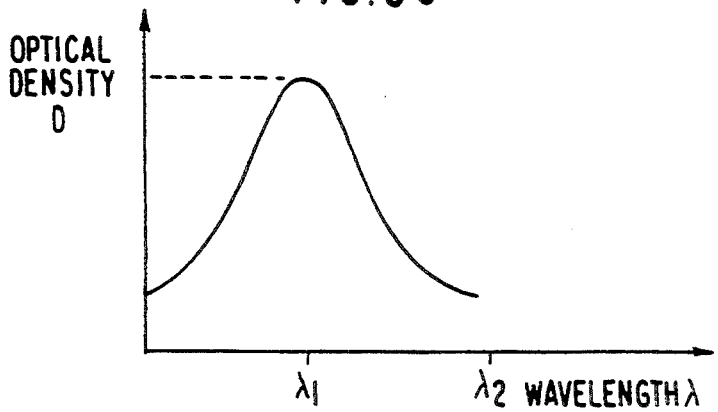

The dual-wavelength approach is superior to the single-wavelength approach because if measurements are done on only a single wavelength, and artifacts are present, as can be seen from a comparison of FIG. 5A with FIG. 5C, the spectra will show a higher optical density than actually is present in the solution. By taking the measurements at two different wavelengths, the effects of artifacts can be removed. However, as will be discussed below, the method of the present invention also is effective when a single-wavelength approach is employed.

With the foregoing in mind, the method of the present invention now will be described with reference to FIGS. 6A–6H. Defects which exhibit similar, or preferably equal spectra at both of the wavelengths at which measurements are taken are provided selectively on the bottom of the wells of each microstrip or by introducing a mark chemically into the well, that mark being removed chemically from the well during the protocol through which the automated instrument runs the solution. Presence (absence) of high optical density values may signify a 1, and correspondingly absence (presence) of such values may signify a 0.

Looking at FIGS. 6A and 6B, when artifacts (marks) are placed intentionally on selected wells on a microstrip before addition of a solution (or alternatively when a suitable chemical is introduced into those selected wells before addition of that solution), the spectra at $\lambda_1$ and $\lambda_2$ appear as in those FIGS. Ideally, if the two spectra were subtracted from each other, there would be complete cancellation, as shown in FIG. 6C. However, in a non-ideal situation, there would be some residual, as shown in FIG. 6D. It should be noted that the existence of residual in the dual-wavelength situation would be not unlike the case of the single-wavelength situation, as will be explained below.

When the solution is added to the wells, assuming the existence of residual spectra as described with reference to FIG. 6D, the spectra change, so that at the end of the reaction or series of reactions which are performed during the given protocol, the results, for wavelength $\lambda_1$ would be as shown in FIG. 6E. Subtracting FIG. 6D from FIG. 6E would yield the results shown in FIG. 6F.

Since in the example being described there are eight wells per microstrip, it is possible to form an 8 bit binary representation corresponding to a particular analyte for which the test is to be conducted. For example, the 8 bit sequence [1 0 1 0 1 0 1 0] may correspond to a strip which is treated with samples which are to be tested for chlamydia, and the 8 bit sequence [0 0 0 0 1 1 1 1] may correspond to a strip which is treated with samples which are to be tested for HIV. Alternatively, the first and eighth bits may be used to set threshold levels of lightness and darkness of the mark, one bit always being 1 and the other always being 0. The remaining 6 bits then can be used to identify diseases being tested for. With a 6 bit representation, each bit having one of two possible states, it is possible to encode $2^6 = 64$ different analytes; with an 8 bit representation, it is possible to encode $2^8 = 256$ different analytes.

The invention is equally applicable to different types of microstrips, as mentioned above. Thus, it would be possible, given that different microstrips have different numbers of wells, in a single-row or a double-row configuration, to have different lengths of binary code representations.

The optical defect may be introduced in a number of ways. For example, it may be done through offset printing, hot stamping, or laser marking. The mark may be placed either in the center of the well or off center. For markings on center, if the defects are placed such that they have the same effect for both wavelengths for which measurement is taken, the effect on the test results can be cancelled out when the final computation is made. However, even if the marking does not have the same effect at both measurement wavelengths, the difference can be accounted for and stored in memory, so that during final testing, the difference can be removed, or subtracted from the final results, thus greatly reducing the effect of having defects on the bottom of the wells.

A similar approach can be taken when a single-wavelength technique is used. The results would look similar to those of FIG. 6D, in that there would be some residual. However, such a residual could be stored as a known value, and subtracted from the final results, thus reducing the effect of the defects as in the dual-wavelength case described immediately above.

Figure 2A:
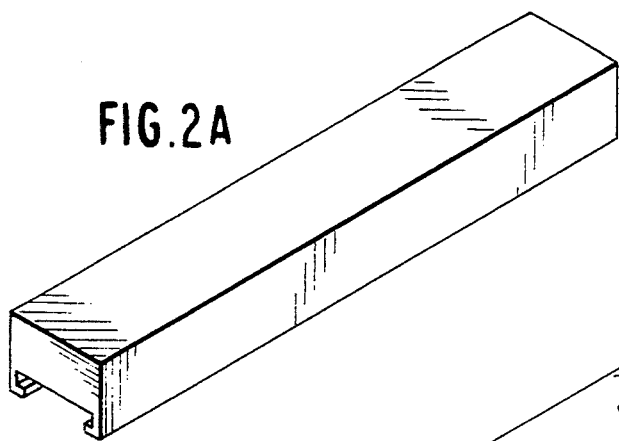
FIG. 2A shows a sample of a conventional microstrip holder.
Figure 2B:
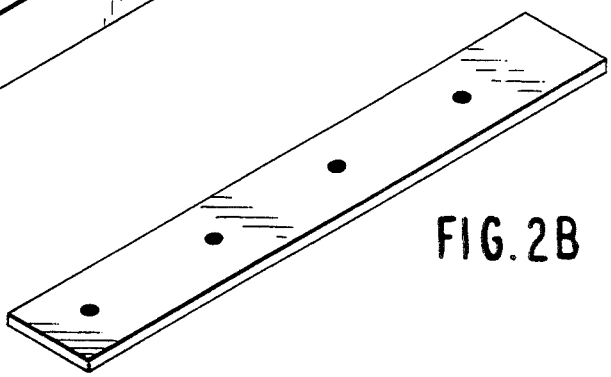
FIG. 2B shows a holder on which appropriate indications are provided, again in accordance with the method of the present invention.

As an alternative to marking the microstrip itself, a microstrip holder can be marked. An example of an unmarked holder is shown in FIG. 2A, and a marked holder is shown in FIG. 2B. The same reading technique could be applied, except that the reading off the microstrip holder would not necessarily have an effect on the reading of the microstrip itself during the actual test.

For defects placed off center, the initial detection and identification of the strip can be done by placing the strip off center, reading the code, and then moving the strip on center for conducting the actual optical density measurements. Such a technique would be useful for automated instruments which use only a single wavelength measurement. Of course, the single wavelength measurement is inferior to the dual-wavelength measurement, as discussed above, but that inferiority is irrelevant to the utility of the present invention. The mark would be cancelled by employing methods similar to those used in the dual-wavelength technique, but the results would not be as exacting.

In addition to the marking of the microstrip or microstrip holder, as mentioned above, a chemical may be introduced into the solution, to provide a different spectral characteristic.

While the foregoing description has been provided in the context of an example of a microstrip of a particular size, in which optical density was the measured characteristic, the technique of the invention is applicable to other characteristics which may be introduced in microstrips in similar ways. A number of these characteristics have been mentioned above.

Figure 4:
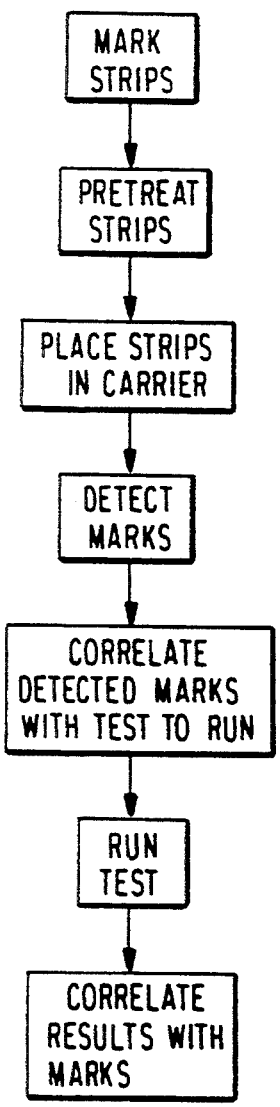
FIG. 4 shows a flow chart of a sequence of events prior to actual conducting of the automated test in accordance with the method of the invention.

A summary of the sequence of identification prior to testing is shown in the flow chart of FIG. 4. Basically, the sequence is as follows:

1. Mark the microstrips in a prearranged pattern corresponding to a binary code, in accordance with a particular analyte with which that strip is to be identified.

2. Place the marked strips into a strip carrier and insert into the testing instrument.

3. Align the strip with the instrument (this may be done by the instrument itself) so that the light path of a known quantity of light passes through each well and is collected and measured.

4. Assign a 0 or a 1 depending on whether a mark is detected.

5. Correlate the detected sequence of zeroes and ones with known sequences to identify the particular analyte.

6. Run the test in accordance with the identified analyte protocol to be tested for.

In a conventional technique, where a user might input the information through a keyboard, the machine would receive the same sort of identification corresponding to the coded input by the user; however, with the present device, with the strip being pre-marked, there is a greatly lessened possibility of error from misidentification of strips, as the user has no part in inputting this information to the tester. This is important because all strips can look the same, even when different analytes are to be tested for.

To assist the user further, it would be possible to mark the bottoms of the wells with letters or numbers, so that the code on the bottom of the wells, is both machine-readable and human-readable.

Having identified the particular microstrip, an appropriate protocol then can be run. Generally, such a protocol would include placement of samples in a microwell plate tray, incubation, washing, dispensing of reagents or antibodies into the solution, and reading of the plate and calculation of results. All of the intermediate reaction, incubation, and dispensing steps may be repeated a number of times in varying sequences, depending on the protocol which the automated instrument would run once it has identified the strips.

While the present invention has been described with respect to one particular embodiment thereof the invention is not to be considered as so limited. Rather, the scope of the invention is to be considered as limited only by the appended claims, which follow immediately.

What is claimed is:

1. A method for distinguishing among strips for different assays in testing by an automated instrument which performs said testing based on detection of one or more physical characteristics to which said automated instrument is sensitive, said method comprising the following steps:

selectively introducing, in a predetermined order, one of said physical characteristics into wells of the microstrip to which the automated instrument is sensitive, said automated instrument correlating said predetermined order to a particular assay; and detecting the presence or absence of said introduced characteristic in each of the wells, wherein the elements of said automated instrument which detect said introduced characteristic perform said testing.

2. A method as claimed in claim 1, wherein said characteristic is optical density.

3. A method as claimed in claim 1, wherein said characteristic is reflectance.

4. A method as claimed in claim 1, wherein said characteristic is radioactivity.

5. A method as claimed in claim 1, wherein said characteristic is luminescence.

6. A method as claimed in claim 1, wherein said characteristic is fluorescence.

7. A method as claimed in claim 1, wherein said selectively introducing step comprises the step of introducing a chemical into selected ones of the microstrip wells to imbue those wells with the characteristic.

8. A method as claimed in claim 1, wherein said selectively introducing step comprises the step of placing on the bottom of the wells a mark having said characteristic.

9. A method as claimed in claim 8, wherein said selectively introducing step further comprises the step of placing said marks away from the center of the bottom of the selected wells.

10. A method as claimed in claim 8, wherein said marks are provided by heat stamping.

11. A method as claimed in claim 8, wherein said marks are provide by offset printing.

12. A method as claimed in claim 8, wherein said marks are provided by laser marking.

13. A method as claimed in claim 8, wherein said selectively introducing step comprises the steps of providing an individual carrier for each of said microstrips, and selectively placing said marks on said individual carrier.

14. A method as claimed in claim 1, wherein said detecting step comprises the step of reading a multi-bit code representative of the test to be conducted.

15. A method as claimed in claim 14, wherein said detecting step comprises the step of reading an 8-bit code representative of the test to be conducted.

16. A method as claimed in claim 14, wherein said detecting step comprises the step of reading a 6-bit code representative of the test to be conducted.

17. A method as claimed in claim 2, wherein said detecting step comprises the step of measuring each of said wells at at least one optical wavelength.

18. A method as claimed in claim 17, wherein said detecting step comprises the step of measuring each of said wells at two different optical wavelengths.

* * * * *